(12) United States Patent
Rakshit et al.

(10) Patent No.: US 10,564,841 B2
(45) Date of Patent: Feb. 18, 2020

(54) ENHANCING INTERACTION WITH A WEARABLE DEVICE

(71) Applicant: International Business Machines Corporation, Armonk, NY (US)

(72) Inventors: Sarbajit K. Rakshit, Kolkata (IN); Martin G. Keen, Cary, NC (US); James E. Bostick, Cedar Park, TX (US); John M. Ganci, Jr., Cary, NC (US)

(73) Assignee: International Business Machines Corporation, Armonk, NY (US)

( * ) Notice: Subject to any disclaimer, the term of this patent is extended or adjusted under 35 U.S.C. 154(b) by 33 days.

(21) Appl. No.: 15/969,990

(22) Filed: May 3, 2018

(65) Prior Publication Data

US 2019/0339853 A1 Nov. 7, 2019

(51) Int. Cl.
| | |
|---|---|
| *G06F 3/0488* | (2013.01) |
| *G06F 1/16* | (2006.01) |
| *G06F 3/0354* | (2013.01) |
| *G06F 3/041* | (2006.01) |
| *A61M 37/00* | (2006.01) |

(52) U.S. Cl.
CPC ..... *G06F 3/04883* (2013.01); *A61M 37/0076* (2013.01); *G06F 1/163* (2013.01); *G06F 3/03545* (2013.01); *G06F 3/03547* (2013.01); *G06F 3/0418* (2013.01)

(58) Field of Classification Search
CPC ...... G06F 3/04883; G06F 3/011; G06F 3/017; G06K 9/00355; G06T 7/248
See application file for complete search history.

(56) References Cited

U.S. PATENT DOCUMENTS

| | | | |
|---|---|---|---|
| 2012/0249409 A1* | 10/2012 | Toney | G06F 3/017 345/156 |
| 2015/0309535 A1* | 10/2015 | Connor | G06F 1/163 361/679.03 |
| 2015/0323998 A1* | 11/2015 | Kudekar | G06F 1/163 345/156 |
| 2016/0091963 A1 | 3/2016 | Kwong et al. | |
| 2017/0131772 A1 | 5/2017 | Choi | |
| 2017/0186286 A1 | 6/2017 | Levesque et al. | |

* cited by examiner

*Primary Examiner* — Kevin M Nguyen
(74) *Attorney, Agent, or Firm* — Schmeiser, Olsen & Watts, LLP; James Nock

(57) ABSTRACT

A system and method may include attaching a wearable device around a wrist of a user, attaching an electronic armband in proximity to an elbow of the user, the electronic armband including a first sensor, attaching a first electronic tattoo to the wearable device and the electronic armband such that the first electronic tattoo extends between the wearable device and the electronic armband, the first electronic tattoo including a second sensor, interacting, by the user, within an interaction control area defined by the wearable device, the electronic armband and the first electronic tattoo, sensing, with the first and second sensors, the interaction in the interaction control area; and providing a communication corresponding to the interaction, by at least one of the first and second sensors, to the wearable device.

20 Claims, 9 Drawing Sheets

ENHANCING INTERACTION WITH A WEARABLE DEVICE

TECHNICAL FIELD

The present invention relates to a wearable system and methods for enhancing interaction with and control of a device. More specifically, the invention relates to a wearable system that detects touching of the skin for enhancing interaction with and control of a device.

BACKGROUND

Over the past decade, the world has seen an explosion of mobile devices such as smart phones and tablets. Now, wearable mobile devices, such as smart watches, are becoming more popular. Smart watches, for example, are becoming more adaptable in social, business and fitness contexts. Despite their rising popularity, user interaction with smartwatches is often limited compared to other devices due to display and screen size. Typical control enhancements, such as keyboards, are not effective in enhancing wearable devices such as smart watches, as users expect to keep both hands free for other operations when interacting and using wearable devices. At present, there are no ideal existing systems or methods for significantly enhancing interaction with and control of a wearable device such as a smart watch. In particular, there is a need for a wearable solution for providing users of wearable devices with a larger multi-functional interaction control area to address the limitations inherent to wearable devices, such as smart watches, of small screen size.

SUMMARY

An aspect of this invention relates to a system that includes: a wearable device configured to be worn around a wrist of a user; an electronic armband configured to be worn in proximity to an elbow of the user, the electronic armband including a first sensor; and a first electronic tattoo configured to be attached to the wearable device and the electronic armband and extend between the wearable device and the electronic armband, the first electronic tattoo including a second sensor, wherein the first and second sensors are configured to sense an interaction by the user within an interaction control area and provide a communication corresponding to the interaction such that the interaction corresponds to a command of the wearable device.

Another aspect of this invention relates to a method that includes: attaching a wearable device around a wrist of a user; attaching an electronic armband in proximity to an elbow of the user, the electronic armband including a first sensor; attaching a first electronic tattoo to the wearable device and the electronic armband such that the first electronic tattoo extends between the wearable device and the electronic armband, the first electronic tattoo including a second sensor; interacting, by the user, within an interaction control area defined by the wearable device, the electronic armband and the first electronic tattoo; sensing, with the first and second sensors, the interaction in the interaction control area; and providing a communication corresponding to the interaction, by at least one of the first and second sensors, to the wearable device.

Another aspect of this invention relates to a computer program product, including a computer readable hardware storage device storing a computer readable program code, the computer readable program code comprising an algorithm that when executed by one or more processors of a computing system implements a method including: receiving, by the one or more processors, a first communication from a first sensor of an electronic armband worn in proximity to an elbow of a user; receiving, by the one or more processors, a second communication from a second sensor of a first electronic tattoo attached to the smart watch and the electronic armband and extending between the wearable device and the electronic armband such that the first electronic tattoo operably couples the smart watch with the electronic armband, wherein the first and second communications correspond to an interaction of the user in an interaction control area defined by the electronic armband, the wearable device and the first electronic tattoo; analyzing, by the one or more processors, the received first and second communications; and performing a command on the wearable device, by the one or more processors, corresponding to at least one of the received first and second communications.

The foregoing and other features of construction and operation will be more readily understood and fully appreciated from the following detailed disclosure, taken in conjunction with accompanying drawings.

BRIEF DESCRIPTION OF THE DRAWINGS

Some of the embodiments will be described in detail, with reference to the following figures, wherein like designations denote like members, wherein.

DETAILED DESCRIPTION

Although certain embodiments are shown and described in detail, it should be understood that various changes and modifications may be made without departing from the scope of the appended claims. The scope of the present disclosure will in no way be limited to the number of constituting components, the materials thereof, the shapes thereof, the relative arrangement thereof, etc., and are disclosed simply as an example of embodiments of the present disclosure. A more complete understanding of the present embodiments and advantages thereof may be acquired by referring to the following description taken in conjunction with the accompanying drawings, in which like reference numbers indicate like features.

As a preface to the detailed description, it should be noted that, as used in this specification and the appended claims, the singular forms "a", "an" and "the" include plural referents, unless the context clearly dictates otherwise.

Current wearable devices, such as smartwatches, include user interfaces in the form of a display screen receptive to the touch of a user wearing the device. The user may use one or more fingers to interact with the display screen and provide touch commands or interactions to the wearable device these touches allow the user to access and utilize the functionality of the wearable device. While these wearable devices allow a user to keep both hands free while wearing the wearable device, the interaction area of these devices is the display screen, which is limited in size. This limited interaction area makes interacting with wearable devices difficult and cumbersome.

Thus, a need exists for systems, methods and computer program products for enhancing interaction with wearable devices. The systems, methods and computer program products described herein may provide enhanced interaction with a wearable device while remaining a wearable solution that provides for hands free operation and interaction with the wearable device.

Figure 1:
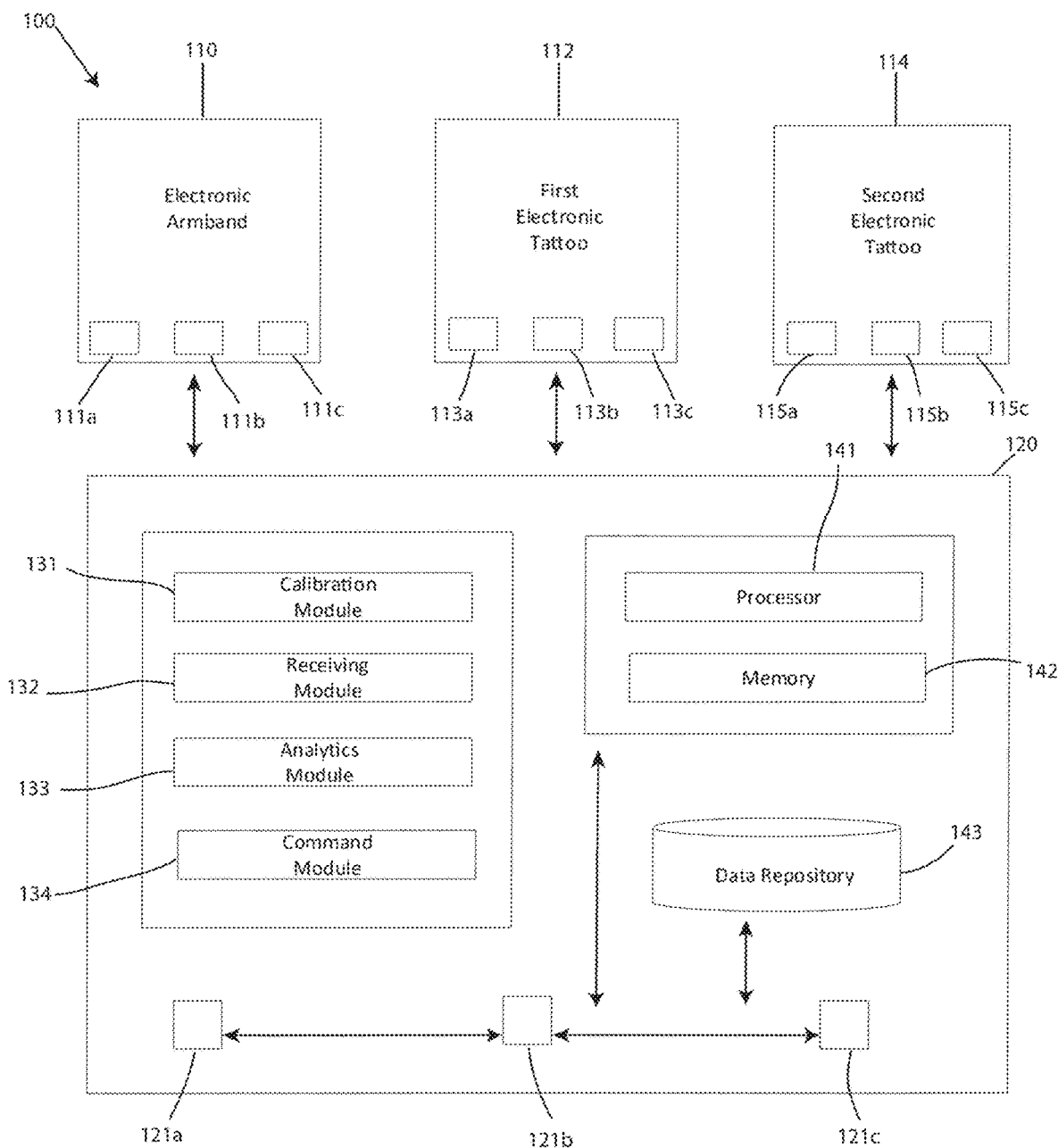
FIG. 1 depicts a block diagram of a system for interacting with a wearable device, in accordance with embodiments of the present invention.

Referring to the drawings, FIG. 1 depicts a block diagram of a system 100 for interacting with a wearable device 120 in accordance with embodiments of the present invention. Embodiments of the system 100 for interacting with the wearable device 120 may be described as a system for enhancing interaction with the wearable device 120, increasing functionality of a wearable device 120, or providing commands to a device such as the wearable device 120. The system 100 for interacting with a wearable device 120 may include the wearable device 120, an electronic arm band 110, a first electronic tattoo 112 and a second electronic tattoo 114. Each of the wearable device 120, the electronic arm band 110, the first electronic tattoo 112 and the second electronic tattoo 114 may be operably connected such that electrical communication can occur there between.

Figure 2:
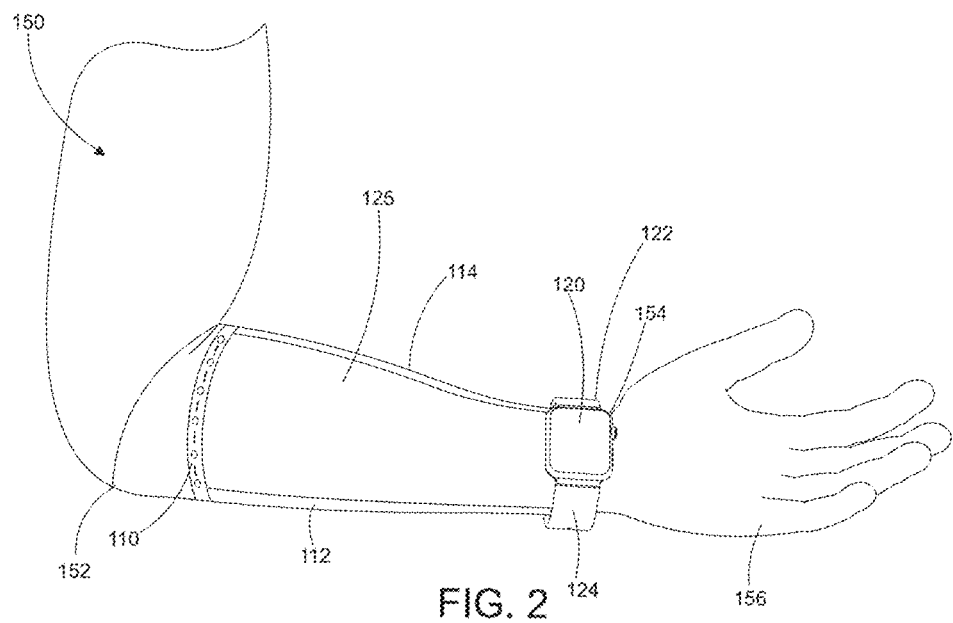
FIG. 2 depicts a perspective view of the system of FIG. 1 being worn by a user, in accordance with embodiments of the present invention.

As shown in FIG. 2, a perspective view of the system 100 for interacting with the wearable device 120 is shown being worn by a user 150 in accordance with embodiments of the present invention. The wearable device 120 may be a smartwatch worn around a wrist 154 of the user 150. The electronic arm band 110 may be worn in proximity to an elbow 152 of the user 150. The first electronic tattoo 112 may be attached, connected or otherwise in electrical communication with each of the electronic arm band 110 and the wearable device 120 such that the first electronic tattoo 112 extends between the electronic arm band 110 and the wearable device 120. Likewise, the second electronic tattoo 114 may be attached, connected or otherwise in electrical communication with each of the electronic arm band 110 and the wearable device 120 such that the second electronic tattoo 114 extends between the electronic arm band 110 and the wearable device 120. The boundary defined by each of the wearable device 120, the electronic arm band 110, and the first and second electronic tattoos 112, 114 may define or create an interaction control area 125. Interactions by the user 150 within the interaction control area 125 may be sensed by the system 100. These interactions may be used to control the wearable device 120, as described herein below.

The wearable device 120 may be a smartwatch or other wearable device configured to be worn around the wrist of the user 150. In other embodiments, the wearable device 120 may be an ankle bracelet, arm band, necklace, or the like. In the embodiment shown, the wearable device 120 may be a smartwatch having a display 122 and a band 124. The display 122 may be a face, screen, pixilated monitor or the like that includes a touch-sensitive user interface. In some embodiments, some or all of the outward facing side of the band 124 may include a touch sensitive user interface and/or display in addition to the display 122. In addition to the interface on the display 122 and the band 124, the wearable device 120 may include one or more physical interaction buttons (not shown). Within the display 122 and/or the band 124 of the wearable device 120 may be included one or more computer processors 141, memory 142 and data repository 143 (shown in FIG. 1). The data repository 143 may be a computer readable storage device coupled to the one or more computer processors 141 containing program code executable by the one or more computer processors 141 via the memory 142 to implement methods for interacting with the wearable device 120 (or the device 210) described herein.

The wearable device 120 may include a plurality of sensors 121a, 121b, 121c configured to be in contact with the wrist 154 of the wearer 150 when worn embedded in either or both of the skin-facing side of the band 124 and the display 122. The sensors 121a, 121b, 121c may be configured to detect movement of the hand and wrist of the user 150. Further, the sensors 121a, 121b, 121c may be configured to detect pressing on the skin of the forearm at particular points when such pressing occurs within the interaction control area 125. While the embodiment shown includes three sensors 121a, 121b, 121c, embodiments are contemplated having more or less than three sensors in the wearable device 120. The wearable device 120 may include various other sensors beyond the pressure or movement sensors 121a, 121b, 121c, such as oximetry sensors, skin conductance sensors, skin temperature sensors, heart rate sensors, accelerometers, gyroscopes, magnetometers and the like. These additional sensors may also be utilized by the wearable device 120 for determining when a user presses on the skin of the forearm in the interaction control area 125. The sensors 121a, 121b, 121c may be in communication with one or more of the processor 141, the memory 142, and the data repository 143 of the wearable device 120. When the sensors 121a, 121b, 121c detect an interaction, the sensors may be able to provide a communication to the processor 141 (either directly or through the data repository 143 and/or memory 142) for analysis. The communication may be a signal, information, data, or the like that may be processed by the processor 141.

The electronic arm band 110 may be an electronic band, braid, tape, binding, cord, harness, strap, string, strip, tie or the like. The electronic arm band 110 may be made of a stretchable material or fabric to accommodate differences in user size. Alternatively, the electronic arm band 110 may include a clasp, buckle, or the like for size adjustment. The electronic arm band 110 may not include a user interface, unlike the wearable device 120. Rather, the electronic arm band 110 may include a plurality of sensors 111a, 111b, 111c configured to be in contact with the skin of the user 150 in an area proximate the elbow 152 as shown. Thus, the forearm of the user 150 may extend between the electronic arm band 110 and the wearable device 120. The sensors 111a, 111b, 111c may be configured to detect movement of the elbow joint of the user 150. Further, the sensors 111a, 111b, 111c may be configured to detect pressing on the skin of the forearm at particular points when such pressing occurs within the interaction control area 125. While the embodiment shown includes three sensors 111*a*, 111*b*, 111*c*, embodiments are contemplated having more or less than three sensors in the electronic arm band 110. The sensors 111*a*, 111*b*, 111*c* may be in communication with one or more of the processor 141, the memory 142, and the data repository 143 of the wearable device 120. In the embodiment shown, a direct connection is made by connecting the electronic arm band 110 to the wearable device 120 through the first and second electronic tattoos 112, 114. When the sensors 111*a*, 111*b*, 111*c* detect an interaction, the sensors may be able to provide a communication to the wearable device 120 for analysis. The communication may be a signal, information, data, or the like that may be processed by the processor 141. The electronic arm band 110 may include a transmitter or transceiver configured to transmit the information gathered by the sensors 111*a*, 111*b*, 111*c*. In some embodiments, the transmitter or transceiver is configured to send this information wirelessly to the wearable device 120 such that no direct connection is needed through the first and second electronic tattoos 112, 114. The electronic arm band 110 may include an internal power source such as a battery that may be rechargeable.

The first and second electronic tattoos 112, 114 may be elongated tattoos, stickers, tape, or the like, that are temporarily attachable to the skin of the user 150. The first and second electronic tattoos 112, 114 may also be referred to as e-tattoos, epidermal electronic devices or epidermal electronics. The first and second electronic tattoos 112, 114 may each be a thin, flexible wearable device that can be adhered to the skin of a wearer, such as the user 150. For example, the first and second electronic tattoos 112, 114 may be less than 3 μm thick. In other embodiments, the first and second electronic tattoos 112, 114 may be less than 1.5 μm thick. In various embodiments, the first and second electronic tattoos 112, 114 may be between 0.5 and 3 μm thick.

The first and second electronic tattoos 112, 114 may each be made of a translucent material and may include thin electrical circuitry therein. The first and second electronic tattoos 112, 114 may each be electrode devices configured to turn the skin of a wearer, such as the user 150, into a digital platform. The first and second electronic tattoos 112, 114 may include an adhesive side configured to be adhered to the skin of a wearer, such as the user 150. The first and second electronic tattoos 112, 114 may each be powered by near-field communications signals emitted from the wearable device 120 or other device (such as the device 210 in the embodiment described herein below). In one embodiment, the first and second electronic tattoos 112, 114 may be disposable once becoming unattached from the user 150 after use. In other embodiments, the first and second electronic tattoos 112, 114 may be reusable.

The first electronic tattoo 112 may include a plurality of sensors 113*a*, 113*b*, 113*c* configured to be in contact with the skin of the user 150 in the interaction control area 125. Likewise, the second electronic tattoo 112 may include a plurality of sensors 115*a*, 115*b*, 115*c* configured to be in contact with the skin of the user 150 in the interaction control area 125. Thus, the sensors 113*a*, 113*b*, 113*c*, 115*a*, 115*b*, 115*c* may be configured to detect pressing on the skin of the forearm at particular points when such pressing occurs within the interaction control area 125. While the embodiment shown includes three sensors for each of the first and second electronic tattoos 112, 114, embodiments are contemplated having more or less than three sensors in the electronic arm band 110. The sensors 113*a*, 113*b*, 113*c*, 115*a*, 115*b*, 115*c* may be in communication with one or more of the processor 141, the memory 142, and the data repository 143 of the wearable device 120. In the embodiment shown, a direct connection is made by connecting the electronic tattoos 112, 114 to the wearable device 120. The first and second electronic tattoos 112, 114 may each include a port, outlet, interface, connector or other physical interface on each end: one for attaching to the wearable device 120, the other for attaching to the electronic arm band 110. Similarly, each of the wearable device 120 and the electronic arm band 110 may include a port, outlet, interface, connector or other physical interface for connecting to each of the first and second electronic tattoos 112, 114. In one embodiment, the first and second electronic tattoos 112, 114 may include male mating interfaces, while the wearable device 120 and the electronic arm band 110 may include a female electronic receiver or port for receiving a connector of the first and second electronic tattoos 112, 114. When the sensors 113*a*, 113*b*, 113*c*, 115*a*, 115*b*, 115*c* detect an interaction, the sensors may be able to provide a communication to the wearable device 120 for analysis. The communication may be a signal, information, data, or the like that may be processed by the processor 141. The first and second electronic tattoos 112, 114 may include a transmitter or transceiver configured to transmit the information gathered by the sensors 113*a*, 113*b*, 113*c*, 115*a*, 115*b*, 115*c*. In still other embodiments, each of the electronic arm band 110, and first and second electronic tattoos 112, 114 may be able to communicate wirelessly by, for example, a wireless transceiver, NFC, or the like, for transmitting information wirelessly to the wearable device 120.

While the embodiment shown includes two electronic tattoos 112, 114 extending between the wearable device 120 and the electronic arm band 110, various other embodiments are contemplated. For example, a single electronic tattoo may extend along a middle point of the forearm between the electronic arm band 110 and the wearable device 120. The single electronic tattoo may be configured to detect pressure and interaction to both sides of the point at which the single electronic tattoo extends. In another embodiment, a large electronic tattoo may extend over the entirety of the interaction control area 125 (rather than the two strip-tattoos in the embodiment shown). Still additional embodiments may include three or more strips spaced apart bordering and/or within the interaction control area 125. In still other embodiments, no electronic arm band may be required, but rather the electronic tattoos may be the only additional components to the system beyond the wearable device.

Figure 3:
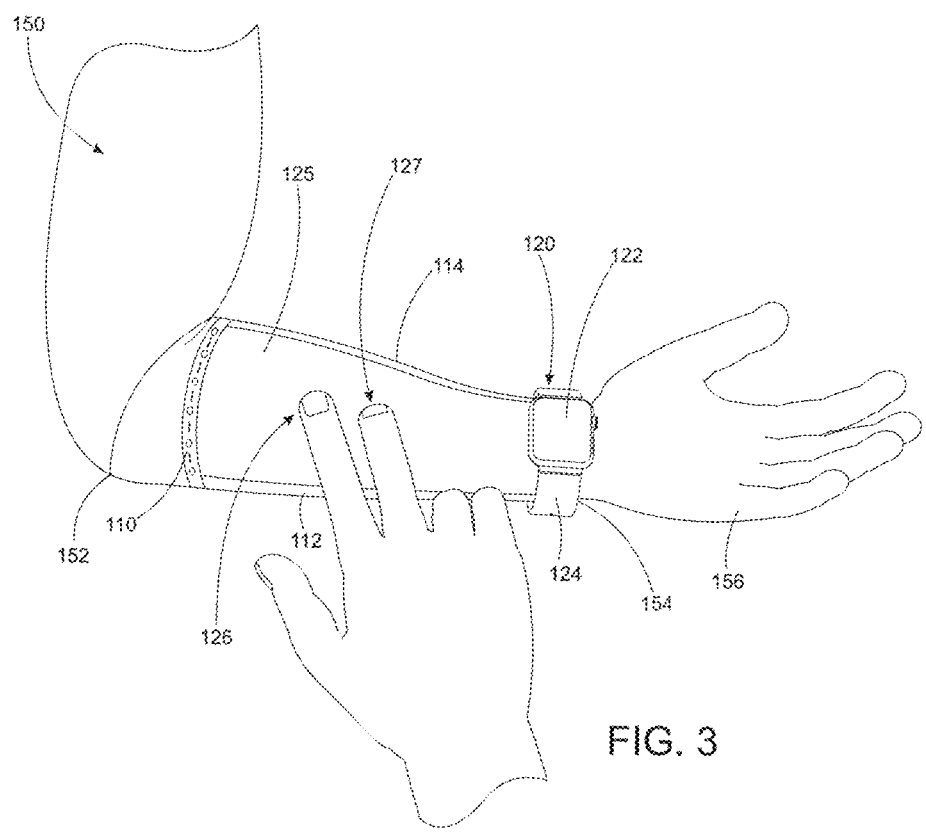
FIG. 3 depicts a perspective view of the system of FIGS. 1-2 being used to control a wearable device, in accordance with embodiments of the present invention.

Referring now to FIG. 3, a perspective view of the system 100 being used by the user 150 to control the wearable device 120 is depicted, in accordance with embodiments of the present invention. When the system 100 is worn by the user 150 or otherwise deployed, the user may interact in the interaction control area 125. These interactions may correspond to commands or functions within the wearable device 120, or other device (such as the device 210 of FIG. 4). In the shown embodiment, the user 150 is shown applying pressure at a first location 126 by a pointer finger and a second location 127 by a middle finger. Thus, the system 100 may be configured to analyze and determine that multiple interactions are occurring simultaneously, in one embodiment.

Referring back to FIG. 1, embodiments of the computer system 120 may be equipped with a memory device 142 which may store data related to calibration, command mapping, interactions, communications from the various devices of the system 100 and the like (as described herein below), and a processor 141 for implementing tasks associated with the system 100 for interacting with the wearable device 120. Embodiments of the wearable device 120 may include a calibration module 131, a receiving module 132, an analytics module 133, and a command module 134. A "module" may refer to a hardware based module, software based module, or a module may be a combination of hardware and software. Embodiments of hardware based modules may include self-contained components such as chipsets, specialized circuitry and one or more memory devices, while a software-based module may be part of a program code or linked to the program code containing specific programmed instructions, which may be loaded in the memory device of the wearable device 120. A module (whether hardware, software, or a combination thereof) may be designed to implement or execute one or more particular functions or routines.

Embodiments of the wearable device 120 may include the calibration module 131. The calibration module 131 may include one or more components of hardware and/or software program code for calibrating, adjusting, regulating, attuning, positioning, and/or sequencing the system 100. Once the wearable device 120, the electronic arm band 110 and the electronic tattoos 112, 114 of the system 100 are in place, the calibration module 131 may be configured to ensure that the devices are in the proper position to sense interaction or pressure against the skin of the user 150 within the interaction control area 125. The calibration module 131 may use one or more trigonometrical equations in order to calibrate, adjust, regulate, attune, position or sequence the devices of the system 100. The calibration module 131 may be configured to determine or detect the size and shape of the interaction control area 125.

In other embodiments, the calibrating module 131 may instruct the user 150 to perform calibration tests by interacting with the interaction control area 125. For example, the calibrating module 131 may instruct the user 150 to apply pressure, with a finger or stylus, to the skin in the middle point of the interaction control area 125. Next, the calibrating module 131 may instruct the user 150 to apply pressure, with a finger or stylus, at each corner of the interaction control area 125, starting with a specified corner. The calibration module 131 may instruct the user 150 to apply moving pressure, with a finger or stylus, to the skin of the forearm in the calibration control area 125, for example, down the length of the forearm at a middle lengthwise position of the calibration control area 125. Likewise, the calibration module 131 may instruct the user 125 to apply moving pressure, with a finger or stylus, to the skin of the forearm in the calibration control area 125, for example, across the forearm at a middle lengthwise position of the calibration control area 125. Thus, the calibration control module 131 may instruct the user 150 to perform an act of writing with a finger or stylus in the interaction control area 125 in the manner guided by the wearable device 120. The calibration control module 131 may instruct the user 150 to perform an act of touching multiple locations in the interaction control area 125 with a finger or stylus in the manner guided by the wearable device 120. The calibration control module 131 may instruct the user 150 to perform an act of drawing symbols in the interaction control area 125 with a finger or stylus in the manner guided by the wearable device 120. For example, the calibration control module 131 may instruct the user 150 to draw a circle, a square, a rectangle, a letter, a number, or the like. Various other instructions may be provided by the calibration control area 125 until it is determined that the system 100 is properly calibrated and sensing pressure within the calibration control area 125 properly and accurately. Calibration by the calibration module 131 may be scaled such that interaction control points or symbols are the same but scaled depending upon how far apart the surrounding wearable devices 110, 112, 114, 120 are located and the size of the calibration control area 125.

In the event that the system 100 had been previously calibrated, the calibrating module 131 may use the one or more processors 141 to guide the user 150 to move at least one of the wearable device 120, the electronic arm band 110, the first electronic tattoo 112 and the second electronic tattoo 114 to a location corresponding to a prior calibrated use. The calibration module 131 may continue to instruct the user 150 to move the devices 110, 112, 114, 120 until the location of the devices 110, 112, 114, 120 corresponds to the previously calibrated use. The calibration module 131 may sequentially calibrate each device separately. In one embodiment, the calibration module 131 provides instructions processed by the processor 141 such that calibration guiding instructions are provided on the display 122 of the wearable device 120 for the user 150 to see and be guided by.

Embodiments of the wearable device 120 may include the receiving module 132. The receiving module 132 may include one or more components of hardware and/or software program code for retrieving, obtaining, or otherwise receiving information or data from the electronic armband 110, the first and second electronic tattoos 112, 114, or other locations from in the wearable device 120, such as at the data repository 143. The receiving module 132 may include a transceiver and associated software for receiving the communications, information or data from the various sensors 111a, 111b, 111c, 113a, 113b, 113c, 115a, 115b, 115c of the system. The receiving module 132 may further be configured to receive internal communications from the various sensors of the wearable device 120, such as the sensors 121a, 121b, 121c. The receiving module 132 may be configured to provide data or information related to the communications from the sensors 111a, 111b, 111c, 113a, 113b, 113c, 115a, 115b, 115c, 121a, 121b, 121c to the data repository 143. The communications, information and data from the sensors 111a, 111b, 111c, 113a, 113b, 113c, 115a, 115b, 115c, 121a, 121b, 121c received by the receiving module 132 for processing may relate to the interactions sensed or otherwise detected in the interaction control area 125. In one embodiment, all the sensors in the system provide a communication each time an interaction occurs in the interaction control area 125. In other embodiments, the sensors are constantly streaming information to the receiving module 132. In still other embodiments, only sensors proximate the interaction in the interaction control area 125 may send a communication for the interaction.

Embodiments of the wearable device 120 may further include an analytics module 133 for analyzing the communications, information and/or data received by the receiving module 132. Embodiments of the analytics module 133 may refer to configurations of hardware, software program code, or combinations of hardware and software programs, capable of analyzing the data and information received from the receiving module 132 and/or the electronic armband 110, the first and second electronic tattoos 112, 114, or other locations from in the wearable device 120 and applying one or more data models to determine the nature of the interaction by the user 150 in the interaction control area 125. The analytics module 133 may rely on applications of statistics, computer programming, and the like, of the data, information and/or communications received by the receiving module 132 and provided to the analytics module 133 in order to determine the nature of the interaction by the user 150 in the interaction control area 125.

The analytics module 133 may be configured to determine the nature of the interaction by the user 150 in the interaction control area 125. For example, based on the information gathered by the sensors 111a, 111b, 111c, 113a, 113b, 113c, 115a, 115b, 115c, 121a, 121b, 121c of the system, the analytics module 133 may be configured to determine that the user 150 touched one or more locations within the interaction control area 125. Likewise, based on the information gathered by the sensors 111a, 111b, 111c, 113a, 113b, 113c, 115a, 115b, 115c, 121a, 121b, 121c of the system, the analytics module 133 may be configured to determine that the user 150 wrote with a finger or stylus within the interaction control area 125. Similarly, based on the information gathered by the sensors 111a, 111b, 111c, 113a, 113b, 113c, 115a, 115b, 115c, 121a, 121b, 121c of the system, the analytics module 133 may be configured to determine that the user 150 wrote a symbol within the interaction control area 125. For example, the analytics module 133 may determine that the user 150 wrote a circle, a square, a rectangle, a letter, a number, or the like within the interaction control area 125. The analytics module 133 may be configured to determine the user 150 interacted, applied pressure, or the like, in a particular location within the interaction control area 125.

Figure 4:
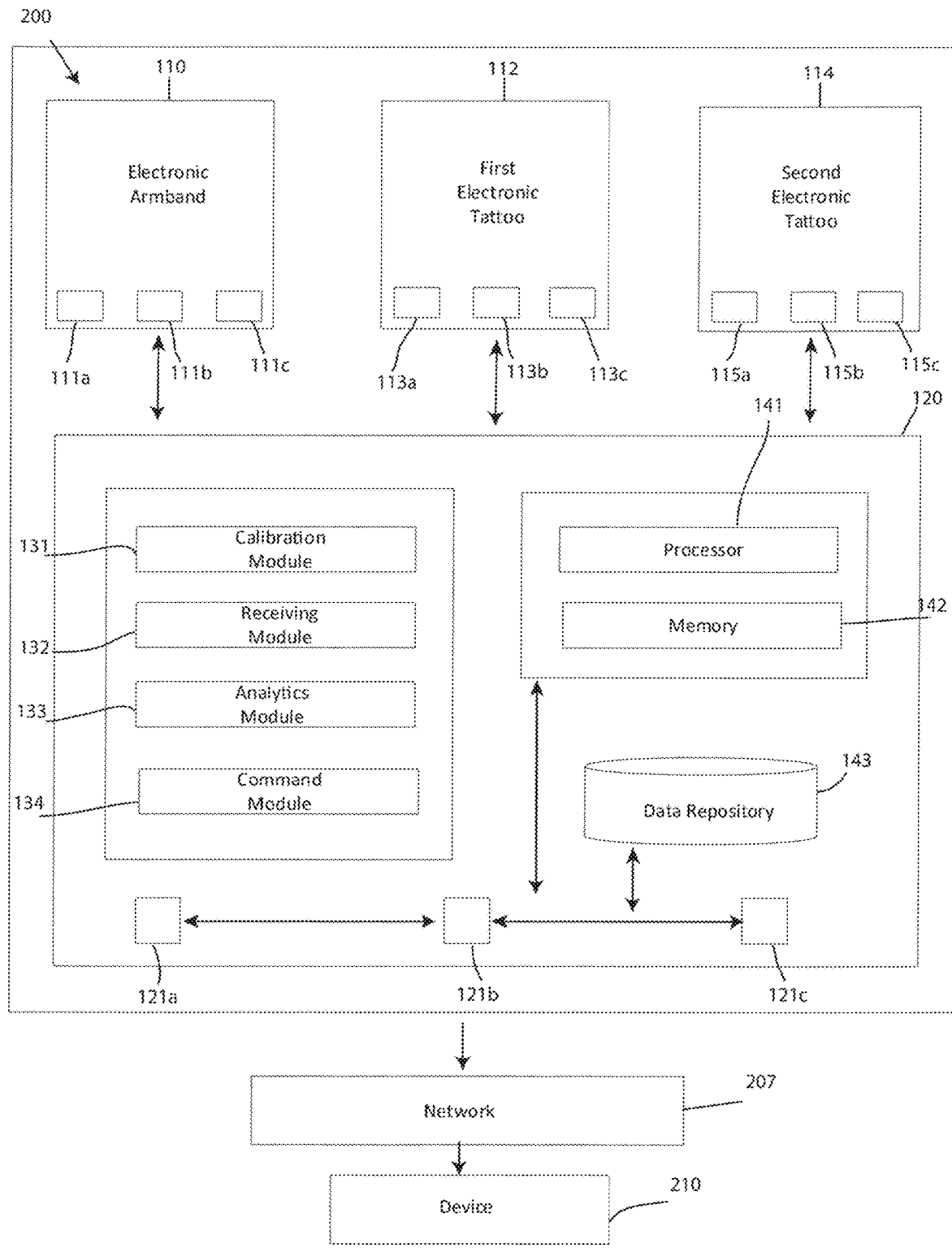
FIG. 4 depicts another system for interacting with a device, in accordance with embodiments of the present invention.

Once the information provided by the sensors 111a, 111b, 111c, 113a, 113b, 113c, 115a, 115b, 115c, 121a, 121b, 121c has been analyzed and the nature of the interaction by the user 150 has been determined, the analytics module 133 may be further configured to determine whether an interaction corresponds, or is "mapped," to a command, function, operation, program instruction, or the like on the wearable device 120, or another device such as the device 210 (described herein below and shown in FIG. 4). For example, a diagonal line or an "X" symbol or letter may correspond to a "close program" operation on the wearable device 120. A circle may correspond to an "open program" operation on the wearable device. Applying simultaneous pressure in two locations may further be analyzed by the analytics module 133 and may correspond to a command, function or operation of the wearable device 120. For example, a thumb and index finger pressed within the control area may be mapped to the opening of a specific program on the wearable device 120 or device 210. Spreading of the thumb and index finger may be mapped or correspond to a zoom in function or operation of the wearable device 120 or device 210. Narrowing of the thumb and index finger may be mapped or correspond to a zoom out function or operation of the wearable device 120 or device 210. A swipe of the finger or stylus may be mapped or correspond to advancing what is being displayed on the wearable device 120 or device 210. Writing with a finger or stylus may correspond to writing on the wearable device 120 or device 210. For example, a text messaging program may receive as an input in a text block the letters and numbers corresponding to what has been written by the user in the interaction control area 125.

With continued reference to FIG. 1, embodiments of the wearable device 120 may include a command module 134. Embodiments of the command module 134 may include one or more components of hardware and/or software program code for mapping interactions with commands and performing commands. After the interaction has been sensed by the sensors 111a, 111b, 111c, 113a, 113b, 113c, 115a, 115b, 115c, 121a, 121b, 121 and sensed information has been received by receiving module 132 and analyzed by the analytics module 133 to determine the nature of the interaction and whether a corresponding command exists for that interaction, the command module 134 may carry out the corresponding command, function, operation or the like on the wearable device 120 or the device 210 (in the case of the embodiment described herein below with respect to FIG. 4). For example, if the analytics module 133 determines that a user has narrowed the thumb and index finger, the command module may perform the command of zooming out on whatever program is currently running on the wearable device 120 or device 210 (in the case of the embodiment described herein below with respect to FIG. 4).

In the case that the commands are not pre-programmed with the system 100 and are customizable by the user 150, the command module 134 may be used in the process of mapping commands or functions to interactions. This could happen during setup of the system 100. For example, after the interaction has been sensed by the sensors 111a, 111b, 111c, 113a, 113b, 113c, 115a, 115b, 115c, 121a, 121b, 121 and sensed information has been received by receiving module 132 and analyzed by the analytics module 133 to determine the nature of the interaction, the command module 134 may be utilized to provide potential commands to map the interaction to. The user may choose from the potential commands provided in order to map the particular interaction to the command for future interactions. In this way, the mapping of interactions to commands or functions in the system 100 may be customized by the user 150. In some embodiments, some mapping may come standard with the system 100, while other mapping may be customized by the user 150. Whatever the embodiment, the system 100 may include a plurality of interactions, each mapped to separate commands of the wearable device 120 or device 210 (in the case of the embodiment described herein below with respect to FIG. 4).

Referring now to FIG. 4, another system 200 for interacting with a device, such as the device 210, is shown. The device 210 may be a mobile phone, tablet, touchpad, laptop, automobile control interface touchpad or navigation system, or the like. In still other embodiments, the device 210 may be a television, video player device, remote control, cable box or the like. For example, a user may be able to control their television, video player device, or automobile control interface, through interactions in the interaction control area 125. In some embodiments, the smartwatch may be connectable to various other Internet of Things (IoT) devices, such as a robotic cleaner, robotic blinds, an HVAC system (or a thermostat thereof), a garage door system, a home monitoring system and the like. When connected, interactions in the interaction control area 125 may be configured to perform functionality on one or more of the various IoT devices. For example, the system 200 may be configured such that when a user interacts by swiping up with three fingers in the interaction control area 125, the wearable device 120 may determine that this is mapped to a command for rising motorized automated blinds in a house. In other embodiments, the system 200 may be configured such that the temperature may be controlled in a house or dwelling with interactions in the interaction control area 125. In still other embodiments, the system 200 may be configured such that garage doors may be opened or closed by interacting in the interaction control area 125. In still embodiments, the system 200 may be configured such that interacting in the interaction control area 125 activates or deactivates a home monitoring system.

In this embodiment, the wearable device 120, the electronic arm band 110 and the first and second electronic tattoos 112, 114 may be connected as described hereinabove in the system 100. However, unlike the system 100, the system 200 may include performing commands on the device 120 instead of the wearable device 120. In this embodiment, the device 120 may be connected to the wearable device 120 via a network 107. The wearable device 120 may be utilized to perform the various functionality described hereinabove. However, after the interaction has been sensed by the sensors 111a, 111b, 111c, 113a, 113b, 113c, 115a, 115b, 115c, 121a, 121b, 121 and sensed information has been received by receiving module 132 and analyzed by the analytics module 133 to determine the nature of the interaction and whether a corresponding command exists for that interaction, the command module 134 may provide, send or transmit a command to the device 210 instead of performing the command on the wearable device 120.

The network 107 may refer to a group of two or more computer systems linked together. Network 107 may be any type of computer network known by individuals skilled in the art. Examples of computer networks 107 may include a LAN, WAN, campus area networks (CAN), home area networks (HAN), metropolitan area networks (MAN), an enterprise network, cloud computing network (either physical or virtual) e.g. the Internet, a cellular communication network such as a GSM or CDMA network, or a mobile communications data network. The architecture of the computer network 107 may be a peer-to-peer network in some embodiments, wherein in other embodiments, the network 107 may be organized as a client/server architecture.

In this embodiment, the wearable device 120, the electronic arm band 110 and the first and second electronic tattoos 112, 114 may be connected as described hereinabove in the system 100. However, unlike the system 100, the system 200 may include performing commands on the device 210 instead of the wearable device 120. In this embodiment, the device 210 may be connected to the wearable device 120 via a network 107. The wearable device 120 may be utilized to perform the various functionality described hereinabove. However, after the interaction has been sensed by the sensors 111a, 111b, 111c, 113a, 113b, 113c, 115a, 115b, 115c, 121a, 121b, 121 and sensed information has been received by receiving module 132 and analyzed by the analytics module 133 to determine the nature of the interaction and whether a corresponding command exists for that interaction, the command module 134 may provide, send or transmit a command to the device 210 instead of performing the command on the wearable device 120.

Figure 5:
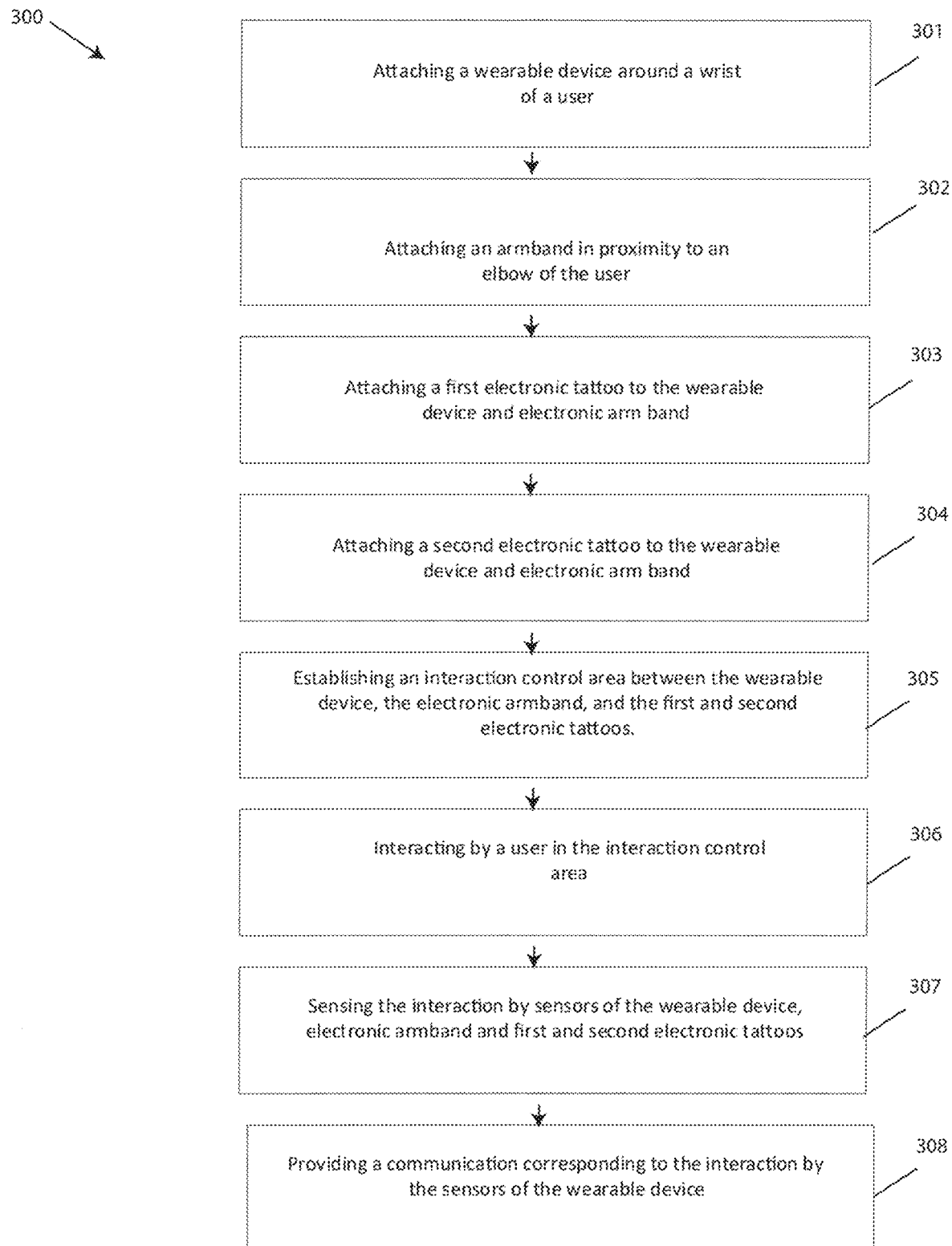
FIG. 5 depicts a flow chart of a method for interacting with a wearable device, in accordance with embodiments of the present invention.

Referring now to FIG. 5, a flow chart of a method 300 for interacting with a wearable device is depicted in accordance with embodiments of the present invention. One embodiment of the method 300 or algorithm may be implemented for interacting with a wearable device in accordance with at least one of the system 100, 200 for interacting with the wearable device 120 described in FIGS. 1-4 using one or more computer systems as defined generally in FIG. 7 below.

Embodiments of the method 300 for interacting with a wearable device may begin at step 301 which includes attaching a wearable device, such as the wearable device 120, around a wrist of a user, such as the wrist 154 of the user 150. The method 300 may include a step 302 of attaching an electronic armband, such as the electronic armband 110, in proximity to an elbow of the user, such as the elbow 152. The electronic armband may include one or more sensors, such as the sensors 111a, 111b, 111c. The method 300 may include a step 303 of attaching a first electronic tattoo, such as the first electronic tattoo 112, to the wearable device and the electronic armband such that the first electronic tattoo extends between the wearable device and the electronic armband. The first electronic tattoo may include one or more sensors, such as the sensors 113a, 113b, 113c. The method 300 may include a next step 304 of attaching a second electronic tattoo, such as the second electronic tattoo 114, to the wearable device and the electronic armband such that the second electronic tattoo extends between the wearable device and the electronic armband. The second electronic tattoo may include one or more sensors, such as the sensors 115a, 115b, 115c. The method may include a step 305 of establishing an interaction control area, such as the interaction control area 125. The interaction control area 125 may be located between the wearable device, the electronic armband, and the first and second electronic tattoos. Thus, the method 300 may include defining the interaction control area to be the outer boundaries of wearable device, the electronic armband and the first and second electronic tattoos. The method 300 may include a step 306 of interacting, by the user, within the interaction control area defined by the wearable device, the electronic armband and the first electronic tattoo. The method 300 may include a step 307 of sensing, with sensors of at least one of the wearable device, the electronic arm band, and the first and second electronic tattoos, the interaction in the interaction control area. The method 300 may include a step 308 of providing a communication corresponding to the interaction, by at least one of the first and second sensors, to the wearable device. The above described steps of the method may be performed in the order listed. In other embodiments, steps of the method 300 may be performed out of the order listed.

Figure 6:
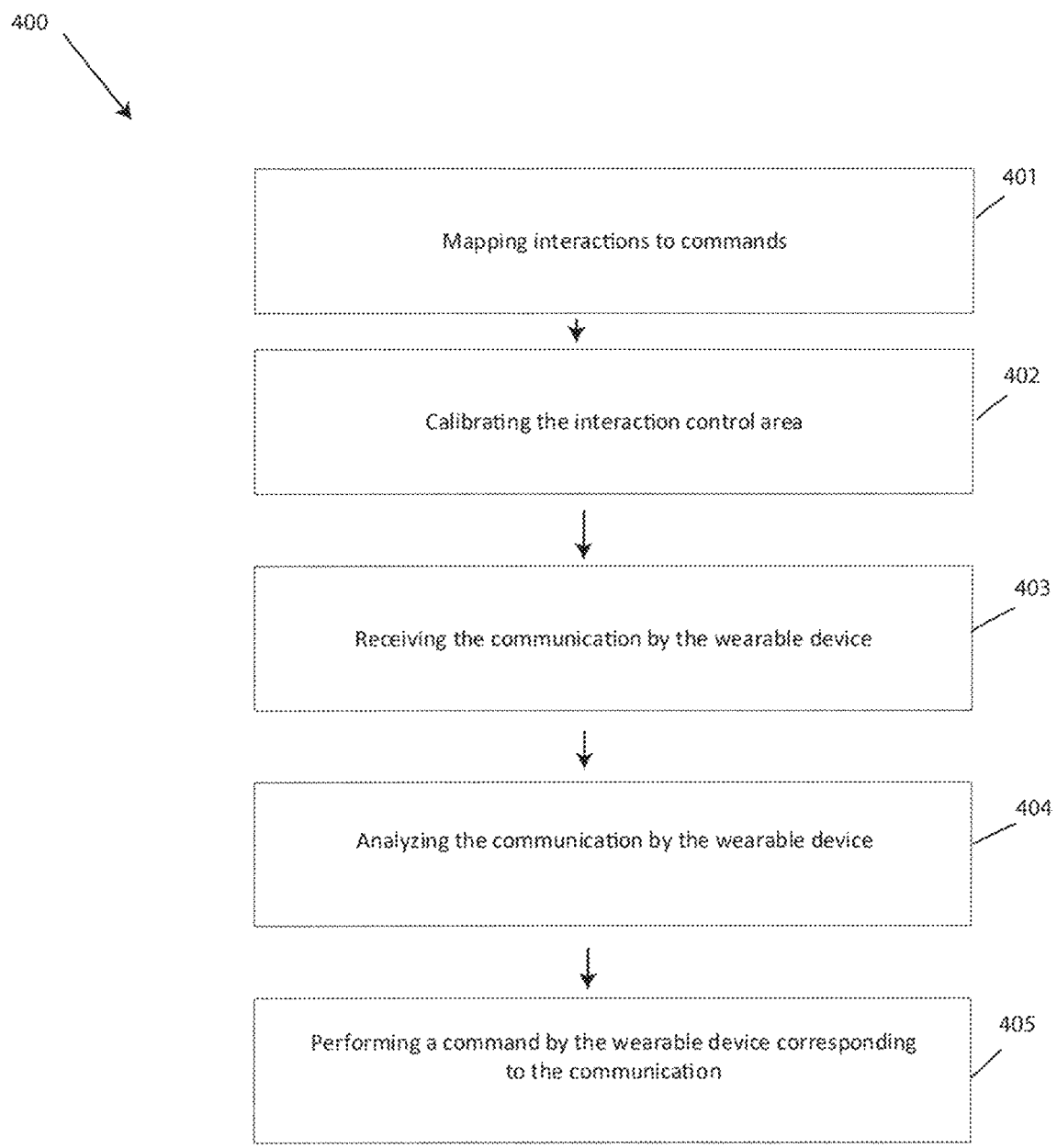
FIG. 6 depicts a flow chart of a method for performing commands on a wearable device, in accordance with embodiments of the present invention.

FIG. 6 depicts a flow chart of a method 400 for performing commands on a device such as a wearable device, in accordance with embodiments of the present invention. In one embodiment, the method 400 constitutes additional steps to the method 300. In other embodiments, steps of the method 400 may be performed separately from steps of the method 300. One embodiment of the method 400 or algorithm may be implemented for interacting with a wearable device in accordance with at least one of the systems 100, 200 for interacting with the wearable device 120 described in FIGS. 1-4 using one or more computer systems as defined generally in FIG. 7 below.

Embodiments of the method 400 for performing commands on a device such as a wearable device may begin at step 401 which includes mapping, by the wearable device, the device 210 or one or more computer processors thereof, a plurality of interactions, each to separate commands of a device such as the wearable device 120 or the device 210. The method 400 may include a step 402 of calibrating, by the wearable device, the device 210 or one or more computer processors thereof, an interaction control area, such as the interaction control area 125. The calibrating may be performed using at least one trigonometrical equation. The calibrating step 402 may further include guiding, by the wearable device, the device 210 or one or more computer processors thereof, the user to move at least one of the wearable device, the electronic armband and the first electronic tattoo to a location corresponding to a prior calibrated use. The calibrating step 402 may further include instructing, by the wearable device, the device 210 or one or more computer processors thereof, the user to perform calibration tests by interacting with the interaction control area. The calibration tests may include instructing, by the wearable device, the device 210 or one or more computer processors thereof, for the user to perform writing with a finger or stylus in the interaction control area in a manner guided by the wearable device, the device 210 or one or more computer processors thereof. The calibration tests may include instructing, by the wearable device, the device 210 or one or more computer processors thereof, for the user to perform touching multiple locations with a finger or stylus in the interaction control area in a manner guided by the wearable device, the device 210 or one or more computer processors thereof. The calibration tests may include instructing, by the wearable device, the device 210 or one or more computer processors thereof, for the user to perform drawing symbols with a finger or stylus in the interaction control area in a manner guided by the wearable device, the device 210 or one or more computer processors thereof. The method 400 may include a step 403 of receiving, by the wearable device, a communication from at least one of the first and second sensors, such as the communication described in step 308 of the method 300. The method 400 may include a step 404 of analyzing, by the wearable device, the device 210 or one or more computer processors thereof, the received communication. The analyzing step 404 may include determining, by the wearable device, the device 210 or one or more computer processors thereof, that the user interacted with the interaction control area in a manner selected from the group consisting of: writing by the user with a finger or stylus; touching or more locations by the user with a finger or stylus, and drawing symbols by the user with a finger or stylus, and combinations thereof. The method 300 may include a step 405 of performing the command, by the wearable device, the device 210 or one or more computer processors thereof, corresponding to the received communication.

Figure 7:
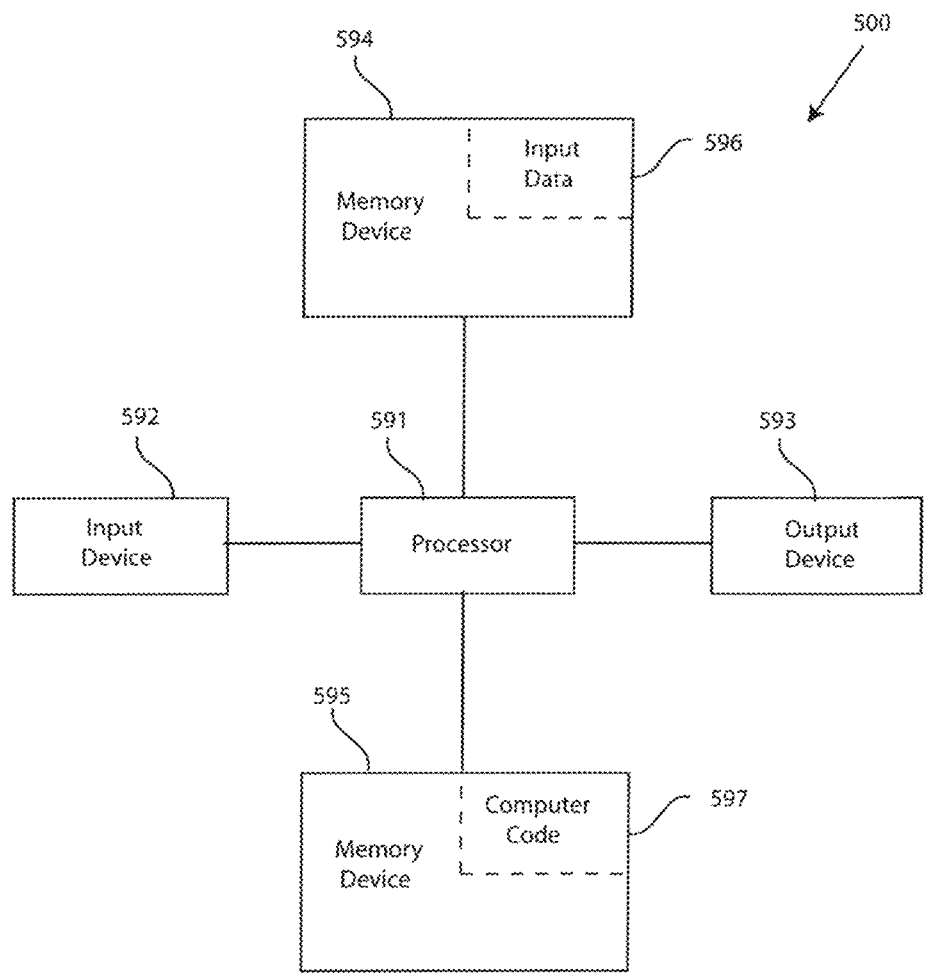
FIG. 7 illustrates a block diagram of a computer system for the systems for interacting with a wearable device of FIG. 1 and FIG. 4, capable of implementing methods for interacting with a wearable device of FIG. 5 and methods for performing commands on a wearable device of FIG. 6, in accordance with embodiments of the present invention.

FIG. 7 illustrates a block diagram of a computer system 500 that may be included in the system of FIGS. 1-4 and for implementing the methods of FIGS. 5-6 in accordance with the embodiments of the present disclosure. The computer system 500 may generally comprise a processor 591, an input device 592 coupled to the processor 591, an output device 593 coupled to the processor 591, and memory devices 594 and 595 each coupled to the processor 591. The input device 592, output device 593 and memory devices 594, 595 may each be coupled to the processor 591 via a bus. Processor 591 may perform computations and control the functions of computer 500, including executing instructions included in the computer code 597 for the tools and programs capable of implementing methods for interacting with a wearable device and performing commands on a device, in the manner prescribed by the embodiments of FIGS. 1-6 using the systems of FIGS. 1-4, wherein the instructions of the computer code 597 may be executed by processor 591 via memory device 595. The computer code 597 may include software or program instructions that may implement one or more algorithms for implementing the methods for interacting with a wearable device and performing commands on a device, as described in detail above. The processor 591 executes the computer code 597. Processor 591 may include a single processing unit, or may be distributed across one or more processing units in one or more locations (e.g., on a client and server).

The memory device 594 may include input data 596. The input data 596 includes any inputs required by the computer code 597. The output device 593 displays output from the computer code 597. Either or both memory devices 594 and 595 may be used as a computer usable storage medium (or program storage device) having a computer readable program embodied therein and/or having other data stored therein, wherein the computer readable program comprises the computer code 597. Generally, a computer program product (or, alternatively, an article of manufacture) of the computer system 500 may comprise said computer usable storage medium (or said program storage device).

Memory devices 594, 595 include any known computer readable storage medium, including those described in detail below. In one embodiment, cache memory elements of memory devices 594, 595 may provide temporary storage of at least some program code (e.g., computer code 597) in order to reduce the number of times code must be retrieved from bulk storage while instructions of the computer code 597 are executed. Moreover, similar to processor 591, memory devices 594, 595 may reside at a single physical location, including one or more types of data storage, or be distributed across a plurality of physical systems in various forms. Further, memory devices 594, 595 can include data distributed across, for example, a local area network (LAN) or a wide area network (WAN). Further, memory devices 594, 595 may include an operating system (not shown) and may include other systems not shown in FIG. 6.

In some embodiments, the computer system 500 may further be coupled to an Input/output (I/O) interface and a computer data storage unit. An I/O interface may include any system for exchanging information to or from an input device 592 or output device 593. The input device 592 may be, inter alia, a keyboard, a mouse, etc. or in some embodiments the sensors 110. The output device 593 may be, inter alia, a printer, a plotter, a display device (such as a computer screen), a magnetic tape, a removable hard disk, a floppy disk, etc. The memory devices 594 and 595 may be, inter alia, a hard disk, a floppy disk, a magnetic tape, an optical storage such as a compact disc (CD) or a digital video disc (DVD), a dynamic random access memory (DRAM), a read-only memory (ROM), etc. The bus may provide a communication link between each of the components in computer 500, and may include any type of transmission link, including electrical, optical, wireless, etc.

An I/O interface may allow computer system 500 to store information (e.g., data or program instructions such as program code 597) on and retrieve the information from computer data storage unit (not shown). Computer data storage unit includes a known computer-readable storage medium, which is described below. In one embodiment, computer data storage unit may be a non-volatile data storage device, such as a magnetic disk drive (i.e., hard disk drive) or an optical disc drive (e.g., a CD-ROM drive which receives a CD-ROM disk). In other embodiments, the data storage unit may include a knowledge base or data repository 125 as shown in FIG. 1.

As will be appreciated by one skilled in the art, in some embodiments, the present invention may be a method; in other embodiments, the present invention may be a system; and in other embodiments, the present invention may be a computer program product. Any of the components of the embodiments of the present invention can be deployed, managed, serviced, etc. by a service provider that offers to deploy or integrate computing infrastructure with respect to systems and methods for interacting with a wearable device and performing commands on devices. Thus, an embodiment of the present invention discloses a process for supporting computer infrastructure, where the process includes providing at least one support service for at least one of integrating, hosting, maintaining and deploying computer-readable code (e.g., program code 597) in a computer system (e.g., computer 500) including one or more processor(s) 591, wherein the processor(s) carry out instructions contained in the computer code 597 causing the computer system to perform methods for interacting with a wearable device and performing commands on a device. Another embodiment discloses a process for supporting computer infrastructure, where the process includes integrating computer-readable program code into a computer system including a processor.

The step of integrating includes storing the program code in a computer-readable storage device of the computer system through use of the processor. The program code, upon being executed by the processor, implements methods for interacting with a wearable device and performing commands on a device. Thus, the present invention discloses a process for supporting, deploying and/or integrating computer infrastructure, integrating, hosting, maintaining, and deploying computer-readable code into the computer system 500, wherein the code in combination with the computer system 500 is capable of performing methods for interacting with a wearable device and performing commands on a device.

A computer program product of the present invention comprises one or more computer readable hardware storage devices having computer readable program code stored therein, said program code containing instructions executable by one or more processors of a computer system to implement the methods of the present invention.

A computer system of the present invention comprises one or more processors, one or more memories, and one or more computer readable hardware storage devices, said one or more hardware storage devices containing program code executable by the one or more processors via the one or more memories to implement the methods of the present invention.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 8:
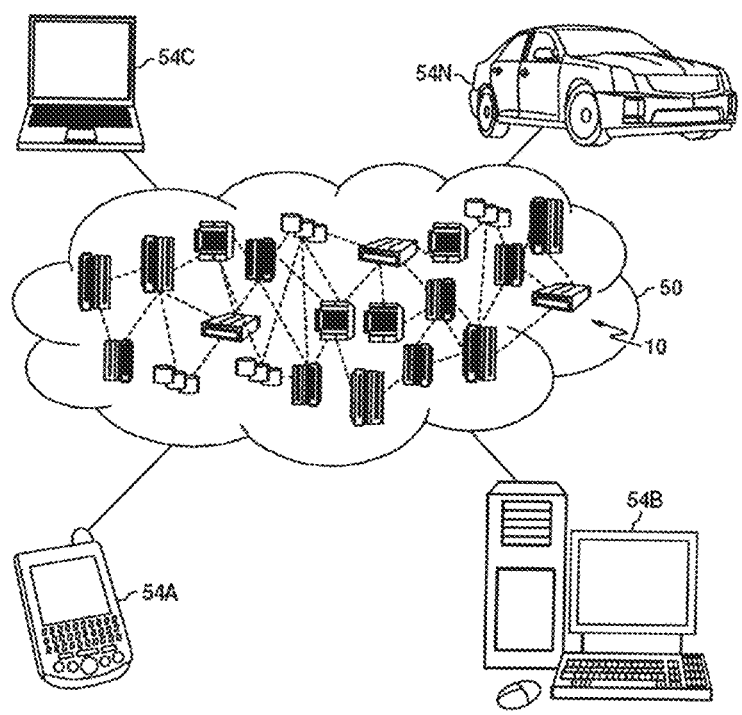
FIG. 8 depicts a cloud computing environment, in accordance with embodiments of the present invention.

Referring now to FIG. 8, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private. Community. Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A, 54B, 54C and 54N shown in FIG. 8 are intended to be illustrative only and that computing nodes 10 and cloud computing environment 50 can communicate with any type of computerized device over any type of network and/or network addressable connection (e.g., using a web browser).

Figure 9:
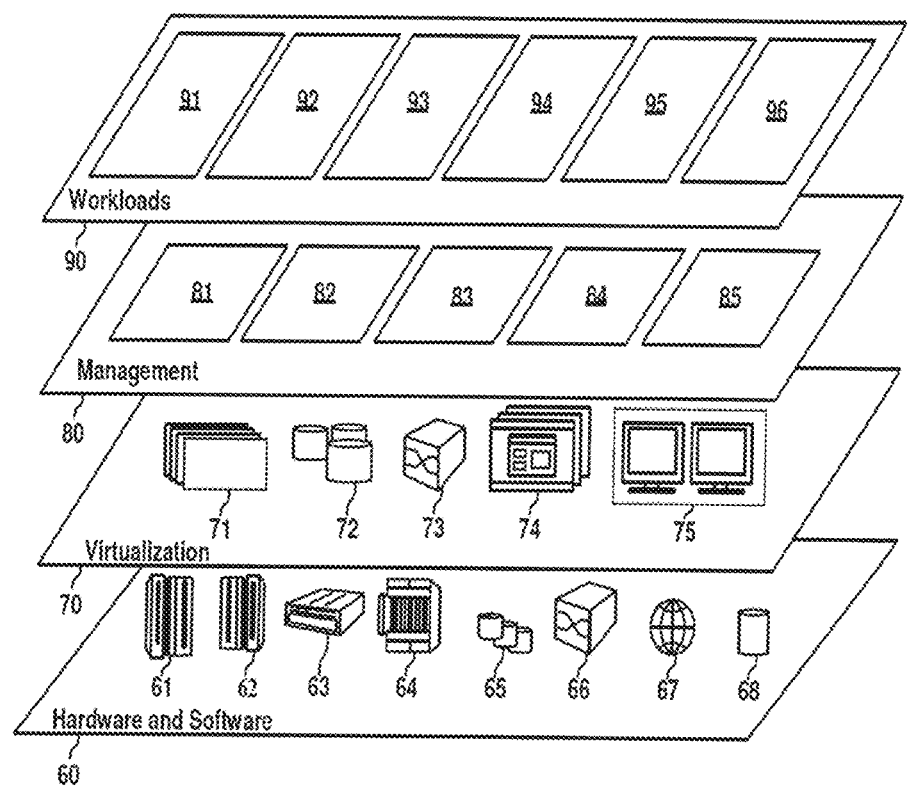
FIG. 9 depicts abstraction model layers, in accordance with embodiments of the present invention.

Referring now to FIG. 9, a set of functional abstraction layers provided by cloud computing environment 50 (see FIG. 8) is shown. It should be understood in advance that the components, layers, and functions shown in FIG. 8 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and ratings generation for entertainment content 96.

While embodiments of the present invention have been described herein for purposes of illustration, many modifications and changes will become apparent to those skilled in the art. Accordingly, the appended claims are intended to encompass all such modifications and changes as fall within the true spirit and scope of this invention.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein

What is claimed is:

1. A system comprising:
   a wearable device configured to be worn around a wrist of a user;
   an electronic armband configured to be worn in proximity to an elbow of the user, the electronic armband including a first sensor; and
   a first electronic tattoo configured to be attached to the wearable device and the electronic armband and extend between the wearable device and the electronic armband, the first electronic tattoo including a second sensor,
   wherein the first and second sensors are configured to sense an interaction by the user within an interaction control area and provide a communication corresponding to the interaction such that the interaction corresponds to a command of the wearable device.

2. The system of claim 1, further comprising a second electronic tattoo configured to be attached to the wearable device and the electronic armband and extend between the wearable device and the electronic armband, the second electronic tattoo including a third sensor, wherein the third sensor is configured to sense the interaction in the interaction control area.

3. The system of claim 1, wherein the wearable device further comprises:
   one or more processors;
   one or more memory devices coupled to the one or more processors; and
   one or more computer readable storage devices coupled to the one or more processors, wherein the one or more storage devices contains program code executable by the one or more processors via the one or more memory devices to implement a method for interacting with the wearable device, the method comprising:
   receiving, by the one or more processors, a communication from at least one of the first and second sensors, the communication corresponding to the interaction by the user in the interaction control area;
   analyzing, by the one or more processors, the received communication; and
   performing the command, by the one or more processors, corresponding to the received communication.

4. The system of claim 3, the method further comprising mapping a plurality of interactions, each to separate commands of the wearable device.

5. The system of claim 3, the method further comprising calibrating, by the one or more processors, the interaction control area prior to the receiving the communication using a trigonometrical equation.

6. The system of claim 5, wherein the calibrating further comprises at least one of:

guiding, by the one or more processors, the user to move at least one of the wearable device, the electronic armband and the first electronic tattoo to a location corresponding to a prior calibrated use; and instructing, by the one or more processors on a display of the wearable device, the user to perform calibration tests by interacting with the interaction control area.

7. The system of claim 3, the method further comprising determining, by the one or more processors, that the user interacted with the interaction control area in a manner selected from the group consisting of: writing by the user with a finger or stylus; touching one or more locations by the user with a finger or stylus, and drawing symbols by the user with a finger or stylus, and combinations thereof.

8. A method comprising:
attaching a wearable device around a wrist of a user;
attaching an electronic armband in proximity to an elbow of the user, the electronic armband including a first sensor;
attaching a first electronic tattoo to the wearable device and the electronic armband such that the first electronic tattoo extends between the wearable device and the electronic armband, the first electronic tattoo including a second sensor;
interacting, by the user, within an interaction control area defined by the wearable device, the electronic armband and the first electronic tattoo,
sensing, with the first and second sensors, the interaction in the interaction control area; and
providing a communication corresponding to the interaction, by at least one of the first and second sensors, to the wearable device.

9. The method of claim 8, further comprising:
attaching a second electronic tattoo to the wearable device and the electronic armband such that the second electronic tattoo extends between the wearable device and the electronic armband, wherein the wearable device, the electronic armband and the first and second electronic tattoos define outer boundaries of the interaction control area; and
sensing, with the third sensor, the interaction in the interaction control area.

10. The method of claim 8, further comprising:
receiving, by the wearable device, the communication from at least one of the first and second sensors;
analyzing, by the wearable device, the received communication; and
performing the command, by the wearable device, corresponding to the received communication.

11. The method of claim 10, further comprising mapping a plurality of interactions, each to separate commands of the wearable device.

12. The method of claim 10, further comprising calibrating, by the wearable device, the interaction control area prior to the receiving the communication using at least one trigonometrical equation.

13. The method of claim 12, wherein the calibrating further comprises at least one of:
guiding, by the wearable device, the user to move at least one of the wearable device, the electronic armband and the first electronic tattoo to a location corresponding to a prior calibrated use; and
instructing, by the wearable device, the user to perform calibration tests by interacting with the interaction control area.

14. The method of claim 8, further comprising determining, by the wearable device, that the user interacted with the interaction control area in a manner selected from the group consisting of: writing by the user with a finger or stylus; touching one or more locations by the user with a finger or stylus, and drawing symbols by the user with a finger or stylus, and combinations thereof.

15. A computer program product, comprising a computer readable hardware storage device storing a computer readable program code, the computer readable program code comprising an algorithm that when executed by one or more processors of a computing system implements a method comprising:
receiving, by the one or more processors, a first communication from a first sensor of an electronic armband worn in proximity to an elbow of a user;
receiving, by the one or more processors, a second communication from a second sensor of a first electronic tattoo attached to the smart watch and the electronic armband and extending between the wearable device and the electronic armband such that the first electronic tattoo operably couples the smart watch with the electronic armband, wherein the first and second communications correspond to an interaction of the user in an interaction control area defined by the electronic armband, the wearable device and the first electronic tattoo;
analyzing, by the one or more processors, the received first and second communications; and
performing a command on the wearable device, by the one or more processors, corresponding to at least one of the received first and second communications.

16. The computer program product of claim 15, the method further comprising determining, by the one or more processors, that the user interacted with the interaction control area in a manner selected from the group consisting of: writing by the user with a finger or stylus; touching one or more locations by the user with a finger or stylus, and drawing symbols by the user with a finger or stylus, and combinations thereof.

17. The computer program product of claim 15, further comprising mapping a plurality of interactions, each to a separate command of the wearable device.

18. The computer program product of claim 15, the method further comprising calibrating, by the one or more processors, the interaction control area prior to the receiving the first and second communications using a calculated trigonometrical equation.

19. The computer program product of claim 18, wherein the calibrating further comprises instructing, by the one or more processors on a display of the wearable device, the user to perform at least one calibration test by interacting with the interaction control area, wherein the at least one calibration test includes at least one of:
writing with a finger or stylus in the interaction control area in a manner guided by the one or more processors;
touching multiple locations with a finger or stylus in the interaction control area in a manner guided by the one or more processors; and
drawing symbols with a finger or stylus in the interaction control area in a manner guided by the one or more processors.

20. The computer program product of claim 18, wherein the calibrating further comprises at least one of:
instructing, by the one or more processors on a display of the wearable device, the user to move at least one of the wearable device, the electronic armband and the first electronic tattoo to a location corresponding to a prior calibrated use; and instructing, by the one or more processors on a display of the wearable device, the user to perform calibration tests by interacting with the interaction control area.

\* \* \* \* \*